United States Patent [19]

Audeh

[11] Patent Number: 4,702,814
[45] Date of Patent: Oct. 27, 1987

[54] NON-MECHANICAL BUFFER CIRCULATION APPARATUS FOR ELECTROPHORESIS

[75] Inventor: Zuheir L. Audeh, Brookline, Mass.

[73] Assignee: Center for Blood Research, Boston, Mass.

[21] Appl. No.: 907,405

[22] Filed: Sep. 15, 1986

[51] Int. Cl.[4] ............................................. G01N 27/28
[52] U.S. Cl. ............................... 204/299 R; 204/180.1
[58] Field of Search ........... 204/275, 277, 278, 299 R, 204/301, 302, 306, 180.1

[56] References Cited

U.S. PATENT DOCUMENTS

| | | | |
|---|---|---|---|
| 4,310,408 | 1/1982 | Rose et al. | 204/301 |
| 4,358,358 | 11/1982 | Rhodes | 204/299 R |
| 4,588,491 | 5/1986 | Kreisher et al. | 204/299 R |
| 4,608,146 | 8/1986 | Penaluna | 204/299 R |

Primary Examiner—John F. Niebling
Assistant Examiner—Ben Hsing
Attorney, Agent, or Firm—David Prashker

[57] ABSTRACT

An improvement in electrophoretic apparatus is provided for non-mechanical fluid transfer between the anode and cathode electrode containing chambers of the apparatus. Buffering fluid is transferred from one electrode containing chamber to the other via gas collecting means and a conduit which extends at a positive angle of include between the electrode containing chambers. By providing a constant and uniform rate of fluid transfer, a uniform pH value is maintained throughout the apparatus without use of mechanical pumps for the duration of the electrophoresis.

2 Claims, 1 Drawing Figure

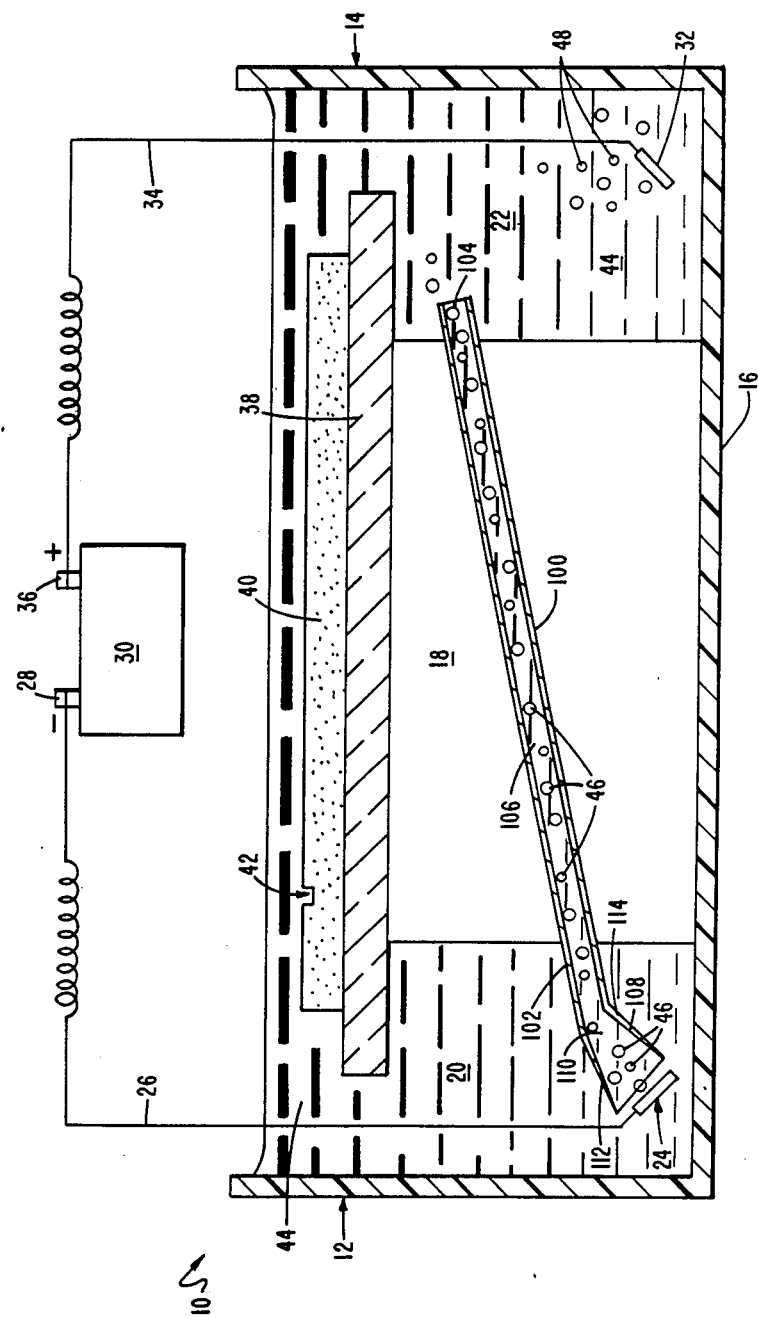

NON-MECHANICAL BUFFER CIRCULATION APPARATUS FOR ELECTROPHORESIS

FIELD OF THE INVENTION

The present invention is generally concerned with apparatus for electrophoresis and is particularly directed to improvements in circulation of buffers and other fluids within electrophoretic apparatus.

BACKGROUND OF THE INVENTION

Many biological polymers are electrically charged and will therefore migrate when placed in an electrical field. One very useful way to separate a mixture of different macromolecules as well as to characterize them is by their rate of movement in an electrical field. This property has been used to determine protein molecular weights; to distinguish among molecules by virtue of their individual net electrical charge; to detect amino acid changes from charged to uncharged residues or vice versa; and to separate different molecular weight species quantitatively as well as qualitatively. The overall technique, apparatus, and theory of such separations has become well established as electrophoresis.

A common used form of electrophoresis is zone electrophoresis, in which a sample is applied as a spot or band and the particles migrate through a solvent that is almost always supported by a homogeneous medium such as paper or a polymerized gel. This type of electrophoresis is used to analyze mixtures of molecules; to determine the purity of a single species of molecule; to assay for changes in mobility and/or confirmation; and for purification and separation of a mixture of different molecules into individual species. More complete and detailed information regarding the basic types of electrophoresis and the many applications for which each type of electrophoresis is utilized may be found in Freifelder, D., *Physical Biochemistry, Applications to Biochemistry and Molecular Biology*, 2nd edition, W. H. Freeman and Compnay, New York, 1982, pages 276–322.

Gel electrophoresis methods and electrophoretic apparatus which utilizes gels such as starch, polyacrylamide, agarose, and agarose-acrylamide as supporting media are well established and highly favored techniques used by investigators in research and industry. Gel electrophoresis provides the user with enhanced resolution and separation of mixtures of macromolecules, particularly proteins and nucleic acids such as deoxyribonucleic acid (hereinafter "DNA") and ribonucleic acid (hereinafter "RNA"). The variety of different applications and the value of gel electrophoresis as a superior analytical and/or preparative tool is demonstrated by the many innovations in apparatus for electrophoresis. These are exemplified by U.S. Pat. Nos. 3,047,489; 4,234,400; 4,151,065; 3,980,546; 3,980,540; 3,932,265; and 3,553,097.

The resolution of DNA and RNA molecules by molecular weight using gel electrophoresis apparatus prominently identifies one of the long standing, recurring problems of electrophoretic analyses. Typically, to obtain a good separation of DNA and other large molecular weight compositions (proteins and nucleic acids), electrophoresis must be performed on an extended time basis, typically 16–24 hours in duration. One of the constant problems of long term electrophoretic analysis is the breakdown of the buffer used to control the pH of the medium due to the formation of acid ($H^+$) at the anode and the formation of base ($OH^-$) at the cathode. This problem is usually resolved by circulating the buffer fluid between the anode containing buffer chamber and the cathode containing buffer chamber using a mechanical pump. While adequate to correct the problem, such external mechanical pumps are typically expensive, awkward to utilize within the limited confines of electrophoretic apparatus, and are subject to mechanical breakdown. For these reasons, it is generally accepted and recognized that any improvement in electrophoretic apparatus which would avoid using an external mechanical pump and yet provide for the circulation of buffer within the apparatus to eliminate pH differences between the anode and cathode chambers, would be regarded as a welcome and substantive advance.

SUMMARY OF THE INVENTION

The present invention provides an improvement in a gel electrophoresis apparatus which comprises a housing having at least two chambers, an anode electrode contained in one chamber and a cathode electrode contained in another chamber, and fluid for electrophoresis in each electrode containing chamber, the improvement comprising gas collection means and a conduit extending at a positive angle of incline from the interior of one electrode containing chamber to the interior of the other electrode containing chamber. Fluid, typically buffer, flows from one electrode containing chamber to the other propelled by the gas generated and collected at one or more electrodes without need for any other mechanical or non-mechanical article or apparatus for fluid circulation.

DETAILED DESCRIPTION OF THE FIGURES

The present invention may be more easily and completely understood when taken in conjunction with the accompanying drawing, in which, FIG. 1 is a cross-sectional view of an electrophoretic apparatus illustrating a preferred embodiment of the present invention.

DETAILED DESCRIPTION OF THE INVENTION

The present invention is an improvement in electrophoretic apparatus which provides means for circulation of fluid such as a buffer of varying pH values and buffering capacities. The present invention comprises gas collection means for capturing and collecting the bubbles of gas generated at the anode and/or cathode respectively; and a conduit in fluid communication with the gas collection means, the conduit extending at a positive angle of incline from the interior of one electrode containing chamber into the interior of the other. Fluid circulation begins almost immediately after each of the respective electrodes is connected to a source of direction electrical current and bubbles of gas are generated at each electrode. The rate of fluid transfer is directly controlled by the rate of gas formation at the respective electrodes.

A preferred embodiment of the present invention is illustrated in FIG. 1 in which a cross-sectional representation of a conventionally known and used gel electrophoretic apparatus employing the present invention is seen. The apparatus illustrated is one mode of performing horizontal gel electrophoresis using a "submarine gel" in which the gel remains submerged within the buffer fluid throughout the entire duration of the electrophoresis. Such apparatus is typically employed for the separation of DNA and RNA by molecular weight using agarose gels. Nevertheless, it will be explicitly understood and recognized that the illustrated apparatus is merely representative of all electrophoretic apparatus in general regardless of specific application and/or regardless whether a gel such as agarose, polyacrylmide, agarose-acrylamide or starch is used as the supporting media; in addition, it is expected and understood that the illustrated apparatus may be modified in a conventionly known al manner for other types of electrophoresis such as paper electrophoresis and cellulose acetate strip electrophoresis without limitation. For descriptive purposes, for clarity, and for ease of comprehension however, the detailed description of the present invention and various embodiments will be directed solely to that apparatus commonly used for submarine gel electrophoresis.

As illustrated by FIG. 1, an electrophoretic apparatus 10 is provided comprising a housing 12 having a plurality of side walls 14 and a base 16. The interior of the housing 12 contains a support block 18, typically composed of plastic or other inert material. Adjacent to the block 18 on both sides are a plurality of buffer chambers 20 and 22. Within the chamber 20 lies a cathode electrode 24 which is in electrical communication via a lead 26 to the negatively charged terminal 28 of a source of direct electrical current 30. Similarly, within the chamber 22 lies an anode electrode 32 which is in electrical communication via a lead 34 to the positive terminal 36 of the direct electrical current power source 30. Disposed upon the top planar surface of the support block 18 is a support plate 38 typically formed of glass. The outer surface of the plate 38 supports a prepared gel medium 40, typically composed of agarose for DNA separations but which may be composed of other compositions or formulations as conventionally used for specific applications. A slot 42 has been made in the gel medium 40 as the site for depositing the sample intended to undergo electrophoresis. The interior void space of the housing 12 is filled with a preselected liquid buffer 44 prepared at known pH and having a predetermined buffering capacity. The choice of liquid buffer 44 for a specific pH value and buffering capacity is conventional and merely a matter of personal choice or convenience with regard to the particular application. With the introduction of electrical current, the cathode and anode electrodes become negatively and positively charged respectively. The sample deposited within the slot 42 will be drawn to the positively charged electrode and will migrate through the gel medium 40 in accordance with the individual net electrical charge and molecular weight of its components.

During normal operation, the buffer 44 will break down and the pH of the fluid in the chambers 20, 22 will be altered by the formation of acid at the anode 32 and by the formation of base at the cathode 24. Typically, as each electrode 24, 32 becomes more highly charged by an increase in electrical voltage, the greater the range of oxygen gas formation and of hydrogen gas formation. The presence of oxygen gas in the chamber 22 and of hydrogen gas in the chamber 20 is visibly identifiable by the gas bubbles 46 and 48 respectively which surround each of the electrodes 24, 32. The described apparatus is that known and conventionally used in this art.

The improvement of the present invention comprises gas collection means, typically a gas trap which captures the gas bubbles generated at an electrode, and a conduit which extends at a positive incline or oblique angle from the interior of the cathode electrode containing chamber into the interior of the anode electrode containing chamber. As illustrated by FIG. 1, a conduit 100 is disposed through the entirety of the support block 18 with the conduits ends 102, 104 extending into the cathode containing chamber 20 and the anode containing chamber 22 respectively. The conduit end 102 expands into a gas trap 108 which overlays and partially envelops the cathode 24. The gas trap 108 is configured substantially as a scoop or hollow wedge and comprises a top surface 110 and two side walls 112, 114. The electric current will charge the cathode 24 and cause the formation of hydrogen gas bubbles 46 which are captured and collected by the gas trap 108. Once within the gas trap 108, the gas bubbles are directed into the interior 106 of the conduit 100. The conduit 100 is a tube formed of plastic or other inert material. The gas bubbles 46 collected by the trap 108 migrate up the positive angle of incline of the conduit interior 106 until released via the conduit end 104 into the chamber 22. The migration of the gas bubbles 46 through the conduit interior 106 concomitantly carriers and propels basic buffer fluid from the chamber 20 through the conduit as an inherent part of the migration process. In this manner, the transfer of liquid from the chamber 20 into the chamber 22 is achieved directly in accordance with the rate of gas bubble migration through the conduit 100. The gas bubbles 46 and basic buffer liquid, having migrated through the entirety of the conduit 100, are released into the acidic (H+ containing) liquid in the anode containing chamber 22 to maintain the desired uniform pH value.

The gas bubble migration and concomitant buffer transfer is empirically demonstrated by using the apparatus illustrated in FIG. 1 under actual test conditions. TAE Buffer (0.04M Tris-acetate; 0.001M EDTA) was prepared to provide a pH value of 8.0. This buffering liquid was added to the chambers 20 and 22 prior to connecting the respective electrodes to the D.C. power source. Upon application of a direct electrical current of 75 volts and 60 milliamperes, the rate of liquid flow from the negatively charged, cathode electrode containing chamber into the positively charged, anode electrode containing chamber was found to be 10±2 milliliters per minute. After allowing the electrophoresis apparatus to operate overnight (approximately 18 hours duration) as the described voltage, the pH value in both electrode chambers was found to be identical at pH 8.0. In comparison, an electrophoretic apparatus similar to that illustrated by FIG. 1, but without fluid communication by any means between the electrode containing chambers was tested. Following electrophoresis at 75 volts and 60 milliampere for approximately 18 hours duration using this conventional apparatus, the pH in the positively charged electrode chamber was 6.2 while the pH at the negatively charged electrode chamber was 10.4. It is therefore unequivocally demonstrated that the present invention provides for fluid transfer and circulation between the electrode containing chambers and maintains a uniform pH value within the apparatus by capturing the gas bubbles generated at one or more charged electrodes, and directing the collected gas bubbles and liquid buffer through one or more conduits into the other electrode chamber.

It will be recognized and appreciated that neither the manner of placement, nor the actual positioning, nor the actual relationship of the gas collection means and the conduit to the respective electrode in each chamber is of consequence or significance. Only three requirements must be met for the invention to be operative: gas collection means capable of capturing and collecting gas bubbles generated at one or more electrodes; at least one conduit for fluid transfer which spatially extends from the gas collection means in each electrode containing chamber and extends into the interior of an other electrode containing chamber; and the presence of each conduit for gas bubble migration and fluid transfer at a positive angle of incline as the conduit extends from the gas collecting means in one chamber into the other chamber. So long as these conditions are met and satisfied, no other features including composition, dimensions, volume, routing positioning, or specific design or addition are meaningful or decisive. It is recognized and expected that many variations in the design and construction of gas collection means and in the routing and positioning of the conduit are possible and desirable for specific applications. Moreover, it is expected that more than one gas collecting trap and conduit in combination will be used within a single electrophoresis apparatus for the purpose of fluid transfer. Since gas bubbles are generated at the cathode and at the anode, gas collection means and conduits can be employed at each electrode concurrently so that buffer flow and transfer will originate from both electrodes simultaneously. Accordingly, it is required only that at least one conduit and gas collection means in combination be present, recognizing that two or more of such combinations will operate more efficiently to achieve the desired goal.

The present invention is not to be limited in form nor restricted in scope except by the claims appended hereto.

What I claim is:

1. In a electrophoresis apparatus including a housing having at least two chambers and a support block to support a sample during electrophoresis, an anode electrode contained in one chamber and a cathode electrode contained in another chamber, and fluid in each electrode containing chamber sufficient to submerge the support block and the sample during electrophoresis, the improvement comprising:

gas collections means for collecting gas bubbles generated at an electrode; and a conduit in fluid communication with said gas collection means, said conduit extending at a positive incline from the interior of one electrode containing chamber into the interior of the other electrode containing chamber of fluid transfer between said chambers.

2. The improved electrophoresis apparatus as recited in claim 1 comprising a plurality of said gas collection means and conduits in combination.

* * * * *